United States Patent [19]

Kearns et al.

[11] Patent Number: 5,573,919
[45] Date of Patent: Nov. 12, 1996

[54] ASSAY USING AN ABSORBENT MATERIAL

[75] Inventors: Kevin Kearns, Lawrenceville; Richard McPartland, Belle Mead, both of N.J.

[73] Assignee: Carter-Wallace, New York, N.Y.

[21] Appl. No.: 66,627

[22] Filed: May 24, 1993

Related U.S. Application Data

[63] Continuation of Ser. No. 610,012, Nov. 5, 1990, abandoned, which is a continuation-in-part of Ser. No. 253,554, Oct. 5, 1988, abandoned, which is a continuation-in-part of Ser. No. 201,584, Jun. 2, 1988, abandoned.

[51] Int. Cl.$^6$ .................... G01N 33/53; G01N 33/542
[52] U.S. Cl. .................. 435/7.9; 435/7.92; 435/7.93; 435/7.94; 436/518; 436/530; 436/533; 436/534; 436/807; 501/80
[58] Field of Search .................... 435/7.1, 7.9, 7.92, 435/7.93, 7.94; 436/513, 518, 530, 533, 534, 805, 807, 810; 422/55–58; 501/80

[56] References Cited

U.S. PATENT DOCUMENTS 3,918,433  11/1975  Fuisz ............................ 128/2
4,366,241  12/1982  Tom et al. ..................... 435/7.1
4,391,904  7/1983  Litman et al. .................. 435/7.1

FOREIGN PATENT DOCUMENTS 0200381  5/1986  European Pat. Off. .

Primary Examiner—Mary E. Mosher
Assistant Examiner—Laurie Scheiner
Attorney, Agent, or Firm—Elliot M. Olstein; Raymond J. Lillie

[57] ABSTRACT

An assay for detecting an analyte which comprises applying a sample containing analyte to a surface of an absorbent material having at least one binder for the analyte supported on at least a portion of the surface. The absorbent material has a porosity which is capable of retaining non-charged particles having a size of at least 0.1 micron and no greater than 10 microns on the surface thereof. The sample flows past the binder and into the absorbent material. Porous plastics or ceramics are preferred absorbent materials.

7 Claims, 2 Drawing Sheets

FIG. 1
FIG. 2
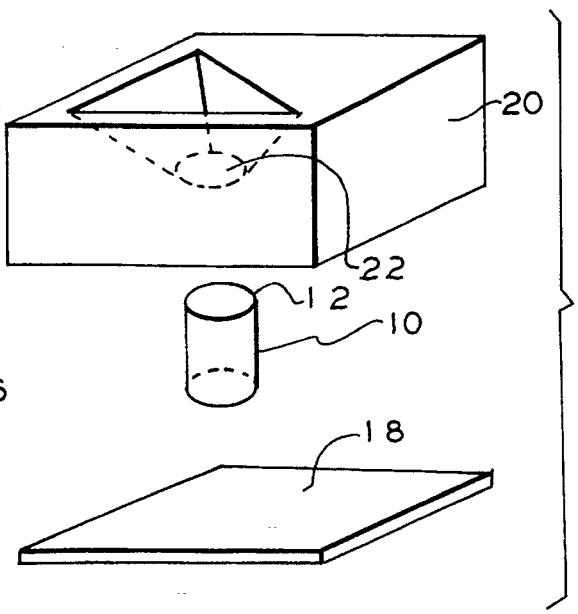
FIG. 3
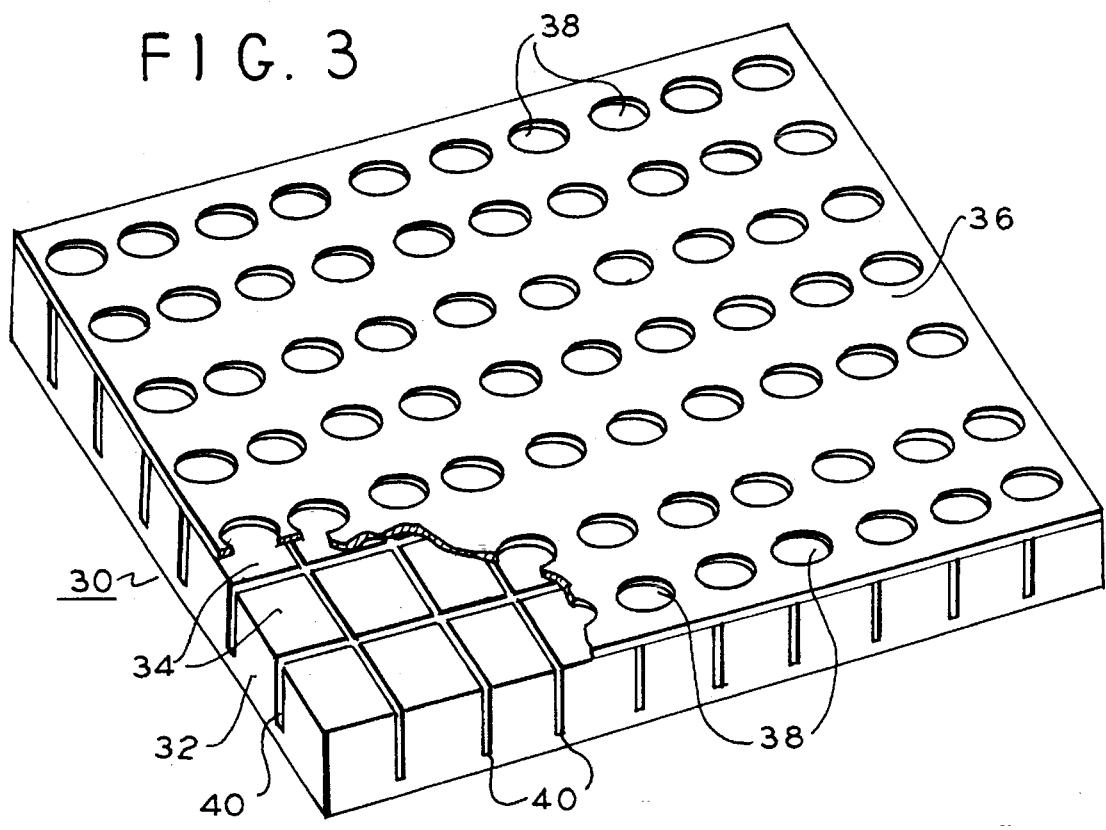

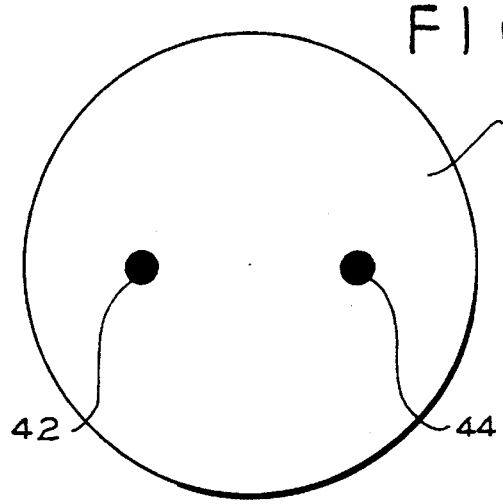
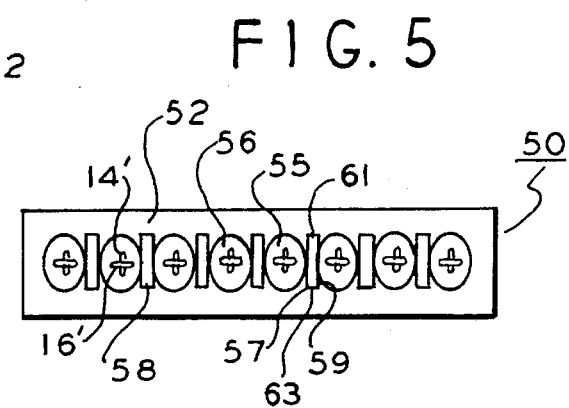
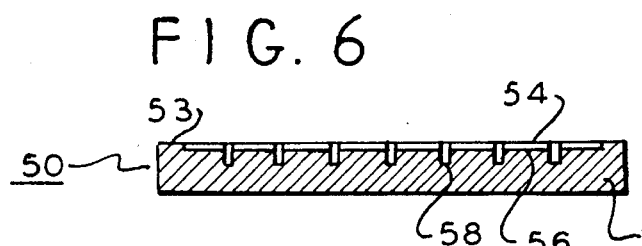
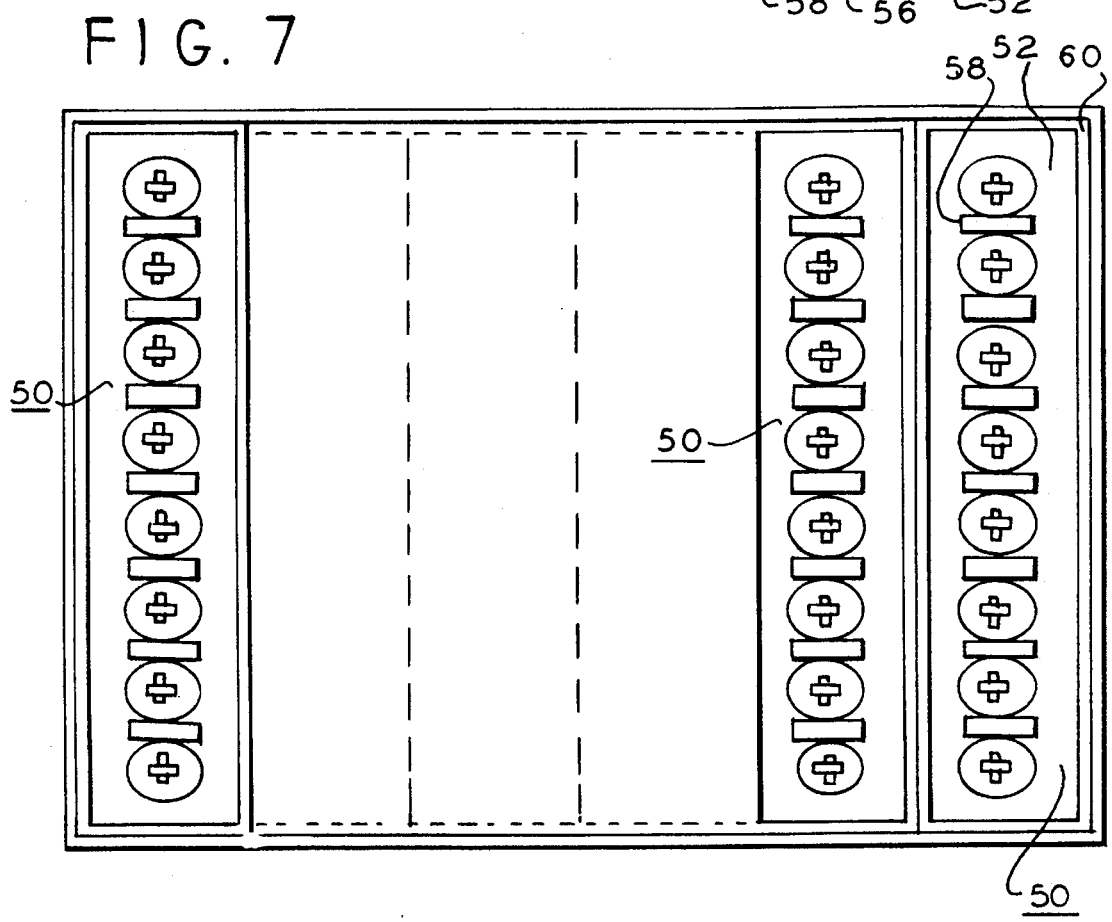

ASSAY USING AN ABSORBENT MATERIAL

This application is a continuation of application Ser. No. 610,012,filed Nov. 5, 1990, now abandoned, wich is a continuation-in-part of application Ser. No. 253,554, filed Oct. 5, 1988, now abandoned, which is a continuation-in-part of application Ser. No. 201,584, filed Jun. 2, 1988,now abandoned.

This application relates to a method of conducting assays, particularly so-called dynamic assays or "flow through" assays. More particularly, this application relates to conducting assays wherein a binder and analyte are contacted on an absorbent material.

It has been known in the art to conduct immunological assays by using an apparatus which contains an absorbent material or an absorbent zone which induces a flow of liquid containing an analyte through a membrane, which supports an antigen, antibody, or other type of binder for the analyte.

U.S. Pat. No. 4,366,241 issued to Tom, et al., discloses a flow-through assay device and assays employing such a device. The assay device has an immunosorbing zone to which is fixed a member of an immunological pair. Located adjacent to the immunosorbing zone is a liquid absorbing zone which draws a liquid sample through the immunosorbing zone. The absorbing zone can control the rate at which the liquid sample is drawn through the immunosorbing zone.

U.S. Pat. No. 4,632,901, issued to Valkirs, et al, discloses an apparatus and process for conducting immunoassays wherein an antibody such as a monoclonal antibody is bound to a membrane or filter. An absorbent material is located below the membrane or filter which induces flow of a fluid sample through the membrane or filter. Analyte in the fluid sample will bind with the antibody on the membrane or filter. Labeled antibody against the analyte may then be added. A washing step then removes unbound labeled antibody. The presence of labeled antibody on the membrane or filter following the washing step is indicative of the presence of analyte in the sample being assayed.

In accordance with an aspect of the present invention, there is provided an assay for an analyte wherein a sample containing analyte is directly applied to an absorbent material on which is supported at least one binder for the analyte. Thus, in the assay, a sample containing analyte is applied to a surface of an absorbent material having at least one binder for the analyte supported on at least a portion of the surface of the absorbent material. The absorbent material employed in the assay is one which is capable of inducing capillary flow whereby liquid applied to a surface thereof is drawn into the absorbent material. In addition, the absorbent material is characterized by a porosity or density whereby the absorbent material is capable of retaining non-charged particles having a size of at least 0.1 micron and no greater than 10 microns on the surface thereof. The sample flows past the supported binder into the absorbent material and analyte is bound by the binder. The analyte bound by the supported binder is then determined. The sample flows past the binder and through the absorbent material by virtue of capillary-type movement through the absorbent material. The absorbent material may be contained within a casing which may be made of plastic. The types of assays intended to be covered within the scope of the invention are known to those of ordinary skill in the art. Such assays include competitive assays, sandwich assays, enzyme-linked immunosorbent (ELISA) assays, agglutination assays, indirect assays, and other assays known in the art.

In accordance with another aspect of the present invention, there is provided a device which comprises an absorbent material which is divided into a plurality of test zones. Each of the plurality of test zones has a surface capable of retaining non-charged particles having a size of at least 0.1 micron and no greater than 10microns. Such a device may be employed in conducting a plurality of assays of the types hereinabove described. The absorbent material of the device enables one to apply sample to each of the test zones in that the absorbent minimizes cross-flow of sample between test zones.

In one embodiment, the device has a cover which has a plurality of openings, each of which is located above a surface of a corresponding test zone. A preferred embodiment of the cover is made of a pressure-sensitive material, such as vinyl, and has die cut openings.

In accordance with another aspect of the present invention, there is a provided a device which is comprised of an absorbent material as hereinabove described. The surface of the absorbent material contains at least one well portion, each of said at least one well portion(s), defining a test zone. The at least one well portion is capable of receiving a sample. Preferably, the surface of the absorbent material contains a plurality of well portions. More preferably, the surface of the absorbent material further includes at least one channel, with each of said at least one channel(s) disposed between two of said plurality of wells. The at least one channel(s) are adapted to receive an overflow of sample which may be applied to a well. Such an embodient may be in the form of a microtiter plate.

The invention will be described with respect to the drawings, wherein:

FIG. 1 is a top view of an embodiment the surface of an absorbent material in accordance with an embodiment of the present invention;

FIG. 2 is an exploded view of a first embodiment of an absorbent material contained within a casing;

FIG. 3 is an isometric view of an alternative embodiment in accordance with the present invention depicting a plurality of test zones;

FIG. 4 is a top view of another embodiment of the surface of an absorbent material in accordance with an embodiment of the present invention;

FIG. 5 is an isometric view of yet another embodiment in accordance with the present invention depleting an absorbent test plate having a plurality of test zones; and FIG. 6 is a cross-sectional view of the embodiment shown in Figure 5; and FIG. 7 is a top view of a plurality of absorbent test plates contained in a tray.

Referring now to the drawings, a solid support in accordance with the present invention may be in the form of a cylinder 10 having a top surface 12. The cylindrical support 10 may be contained within a casing comprised of a bottom portion 18 and a top lid portion 20. The lid 20 of the casing has an opening 22 which surrounds the surface 12 of cylinder 10.

The embodiment shown in FIG. 1 illustrates an embodiment in accordance with the present invention which is known as a plus "+" orminus "−" trap assay. Located on surface 12 of cylinder 10 ne embodiment, are analyte zone 14 and binder zone 16. The analyte and binder may be directly attached to the surface 12 by passive or covalent attachment, or they may be attached to latex particles which are on surface 12. It can be seen that, in this embodiment, analyte zone 14 and binder zone 16 intersect or overlap with each other, thus forming the shape of a plus "+" sign. When one desires to conduct an assay in accordance with this embodiment, one will place the analyte in zone 14 of surface 12, and place a binder for the analyte in zone 16. When one contacts surface 12 with a sample suspected of containing analyte, the analyte, if present, will bind to the binder in zone 16. After the sample is added, the surface 12 is contacted with a tracer having a detectable label, which is bound by the analyte. If analyte is present in the sample, the tracer having the detectable label will bind to both zones 14 and 16. After the surface 12 is subsequently washed, a plus "+" sign will appear on the surface 12 of support 10, thus indicating the presence of analyte. If analyte is not present in the test sample, the tracer having the detectable label will bind only to the analyte in zone 14. The test result will thus be read as a minus "−" sign, thus indicating the absence of antibody to the trap antigen in the sample.

Alternatively, as shown is FIG. 4, there may be located on surface 12 a binder spot 42, which contains a binder for the analyte, and control spot 44, which contains a non-reactive antigen or antibody (e.g., a gamma-globulin). The non-reactive antigen or antibody contained by control spot 44 serves to detect contaminants by trapping non-specific materials. If non-specific binding contaminants are present, such contaminants will bind to the non-reactive or non-specific antibody contained by control spot 44, and develop control spot 44. When sample is applied to the surface 12, analyte, if present, will bind to the binder in binder spot 42, and develop binder spot 42. If analyte is not present, binder spot 42 will not be developed. The binder may be directly attached to surface 12, or may be attached to latex particles which are on surface 12. When latex particles are employed, binder spot 42 includes latex particles to which binder is attached, and control spot 44 includes latex particles to which are attached the non-reactive (i.e., non-specific) antigen or antibody. If a sample containing analyte is applied to surface 12, analyte will bind to the latex particles contained in binder spot 42, and there should be no binding to the particles contained in control spot 44. If analyte is not present in a sample, neither binder spot 42 nor control spot 44 should be developed. If control spot 44 is developed, regardless of whether binder spot 42 is developed, the development of control spot 44 indicates the presence of contaminants in the sample and/or in the testing materials. If control spot 44 is in fact developed upon application of a test sample, the test results should then be disregarded and the presence of analyte should be redetermined using another support.

In an alternative embodiment, shown in FIG. 3, a support 30, made of an absorbent material as hereinabove described is divided into a plurality of test zones 32. Each of the test zones 32 has a surface 34 upon which may be placed binder for the analyte, and, if desired, analyte as well, as hereinabove described, so as to form a binder spot or a "trap" zone. Binder and control spots as hereinabove described can also be placed upon surface 34 as well. The binder, and, if desired, analyte, may be directly attached to surface 34, by passive or covalent attachment, or may be attached to latex particles which are on surface 34. The porosity of the absorbent which makes up the test zones 32 is sufficient to minimize cross-flow of sample from one test zone to another. As a further deterrent to cross-flow between test zones 32, the test zones 32 are separated from each other by a plurality of channels 40 which have been cut into the absorbent material. Thus, this embodiment enables one to carry out a plurality of assays using one device containing a plurality of test zones wherein a sample may be applied to a plurality of the test zones, whereby sample applied to one test zone will not cross-flow to, or contaminate, an adjacent test zone.

Located on the top of support 30 may be a cover 36 having a plurality of openings 38. Each of said openings 38 is located above a surface 34 of a corresponding test zone 32. In a preferred embodiment, cover 36 is made of a pressure-sensitive vinyl having die cut openings.

In yet another embodiment, shown in FIGS. 5 and 6, a support 50 is shown in the form of a microtiter plate, including an absorbent substrate 52 as hereinabove described, into the surface 53 of which are cut a plurality of wells 54, each of said wells 54 defining a test zone. Each of wells 54 is bounded by a circular wall 55. It is to be understood, however, that the shape of wells 54 is not to be limited to a circular shape. A plurality of the supports 50 may be contained within a tray 60.

Each of wells 54 includes a surface 56 to which a sample may be applied. Located on surface 56 is a binder for the analyte, and, if desired, analyte as well. The binder and analyte may be in the form of analyte zone 14' and binder zone 16'. Surface 56 can have, as an alternative, a binder spot and a control spot, as hereinabove described. The binder, and, if desired, analyte, may be attached to surface 56 by passive or covalent attachment, or may be attached to latex particles which are on surface 56. Located between wells 54 are channels 58, each of said channels 58 being bounded by walls 57,59,61 and 63. Each of said channels 58 is adapted to receive overflow of sample applied to an adjacent well 54. Thus, channels 58 serve to provide a space between adjacent wells 54 as well as to prevent cross-flow of samples between adjacent wells 54.

In a competitive assay, an analyte and a tracer compete with a binder specific for the analyte and tracer. The tracer is the analyte or an appropriate analog thereof which is coupled to a detectable label or marker. The tracer and analyte compete for a limited number of binding sites on the binder, and the amount of tracer which is bound to the binder is inversely proportional to the amount of analyte in the sample. The amount of tracer, and the amount of analyte as well, can be determined by measuring the amount of label present. The label or marker which is part of the tracer may be a detectable marker such as a radioactive isotope, of, for example, iodine, cobalt or tritium, an enzyme, a fluorescent dye, an absorbing dye, a chemiluminescent substance, a spin label, biotin, a colored particle or any other labeling substance known to one of ordinary skill in the art. A preferred label is comprised of colored particles such as colloidal gold.

When a sandwich assay is employed, the binder which is specific for an analyte, is contacted with a sample containing or suspected of containing analyte. Analyte present in the sample will bind with the binder. After the sample has flowed past the binder into the absorbent material, the analyte-binder complex is then contacted with a tracer. The tracer is a ligand which is specific for the analyte to be assayed. For example, the tracer can be an antibody elicited in response to the analyte being assayed. The ligand is preferably labeled with a detectable marker as described above, and the amount of analyte present in the sample is determined by the amount of label present on the surface of the absorbent.

In an indirect sandwich assay, analyte bound to the supported binder is contacted with a binder for the analyte which becomes bounded to analyte bound to the supported binder. The tracer used in the assay is a labeled ligand which is bound by the binder bound to the analyte bound to the supported binder.

In an ELISA assay, the tracer or ligand is labeled with an enzyme, and the amount of analyte present in the sample to be assayed is determined by the amount of bound enzyme label present. An ELISA assay may be run as a sandwich assay or a competitive assay.

In an agglutination assay a binder consisting of particles sensitized with an antigen or antibody specific for an analyte is contacted with a sample suspected of containing the analyte. The presence of analytic is evidenced by agglutination of the solid particles.

The binder which is used in the assay in accordance with the present invention is dependent upon the analyte being assayed. For example, of the analyte is an antigen or hapten, the binder may be an antibody or a naturally occurring substance which is specific for the analyte. If the analyte is an antibody, the binder may be an antibody, an antigen, or a naturally occurring substance which is specific for the analyte.

The assay may be employed for determining a wide variety of analytes. Examples of analytes which may be assayed in accordance with the present invention include drugs, hormones, macromolecules, antiboides, microorganisms, toxins, polypeptides, proteins, polysaccharides, nucleic acids, etc. The selection of suitable analyte is deemed to be within the scope of those skilled in the art.

The absorbent material used for the assay in accordance with the present invention may be any absorbent material having a porosity such that it is capable of retaining non-charged particles of at least 0.1 micron and no greater than 10 microns. The absorbent material is wettable (hydrophilic) and provides for capillary movement of liquids through. the absorbent. Although the absorbent material is capable of retaining non-charged particles of at least 0.1 micron and no greater than 10 microns, assays may be conducted using the absorbent material of the present invention without the use of non-charged particles.

The absorbent material used must provide for a proper regulation of flow of the sample through the absorbent. The regulation of flow is important to control the interaction of the specimen with the binder on the surface of the absorbent. Fast flow will cause a loss in sensitivity because the analyte and binder do not have a sufficient time to react. If the flow past the surface and binder is too slow, enhanced nonspecific reactions can occur because nonspecific components in the specimen may not be adequately separated from the binder. Thus, properly regulated flow results in increased assay sensitivity. The absorbent preferably also prevents "back flow" of the sample to the surface of the absorbent. In addition, if the absorbent is divided into a plurality of test zones for performing a multiplicity of assays, the absorbent should prevent or minimize cross-flow of samples between test zones, thereby preventing contamination of sample in one test zone with sample(s) from another test zone(s). When an absorbent is divided into a plurality of test zones, a flow of materials which is too slow, in addition to causing enhanced non-specific reactions, may also cause cross-flow of samples between test zones. An absorbent in accordance with the present invention, and most preferably an absorbent having a porosity within the upper limits of the range hereinabove described, enables the sample to flow downwardly and quickly through the absorbent so as to prevent cross-flow while the speed of such flow is not too excessive such that the assays will have the requisite sensitivity. The absorbent may be housed within a housing or casing made of plastic or of a fiber board.

In a preferred embodiment, the absorbent is a non-fibrous material and in particular an absorbent porous plastic which is "wettable" and capable by itself of providing for capillary flow into the plastic. Examples of non-fibrous plastic absorbent materials which may be used include polyolefin, polyester, porous polyvinyl chloride, and polystyrene. The porous plastic absorbent has a porosity or density as hereinabove described. The porous plastic, in a preferred embodiment, is impregnated with an appropriate material such as a cellulosic material which provides the requisite porosity by filling in the pores of the plastic so as to provide a porous material with the requisite pore sizes as described above. The cellulosic material does not adversely affect the absorbency and wettability of the plastic. A preferred cellulosic material is cellulose acetate. A preferred absorbent material is a porous polyethylene absorbent having a surface containing pores which were constricted by using a cellulosic material. Such a support is sold by Porex Technologies Corp. of Georgia as the MEMPOR™ Porous Plastics Matrix Support System. Porous Plastics Matrix Support System.

The porous plastic may be a hydrophobic porous plastic which is rendered hydrophilic, or wettable, by the addition of a wetting agent such as a surfactant. The surfactant may be applied to all or a portion of the porous plastic material (e.g., after the porous plastic support is impregnated with a cellulosic material ). The plastic, which is hydrophobic, is contacted with a surfactant so as to render and/or a portion of the surface of the porous plastic hydrophilic, or wettable. The binder used in the assay is applied to the "wettable" portion of the porous material. If an insufficient amount of surfactant is applied, the flow rates of specimen and of labeled antibody into the absorbent will be slowed, thus affecting the sensitivity of the assay.

The surfactant may be applied to the entire surface of the support or to a portion of the surface, thus rendering either the entire surface or a portion of the surface hydrophilic.

If one applies the surfactant carefully over the zone where the binder is to be located, the specimen and tracer will be forced to flow into the zones of highest hydrophilicity or wettability where the binder is located. The immunoconcentration mechanism is thereby enhanced, and the flow of specimen across the entire absorbent surface is minimized.

In an alternative embodiment, the absorbent may be in the form of a pressed fiber disc. The pressed fiber is also hydrophilic, or wettable, and capable of providing for capillary flow into the fiber disc. The fiber disc also has a porosity or density which enables the disc to retain non-charged particles having a size of at least 0.1 micron and no greater than 10 microns. The fibers are pressed so as to provide the requisite porosity or density as described above. The surface of the absorbent material which supports the binder is preferably a smooth surface in that it enhances the ability to read tracer on such surface.

The surface of the absorbent material may be coated or treated with a material to prevent non - specific adsorption, e.g., BSA, or any other blocking substance known in the art.

A pressed fiber disc may be made by slurrying fibers and mixing the fibers with an appropriate blocking protein or proteins, buffers, and surfactants. A preferred slurry is comprised of polyester and cellulose acetate. The slurry is poured into a paper press. Excess aqueous material is removed during the pressing stage. The press is operated so as to press the disc to provide a density or porosity of the disc which is sufficient to hold non-charged particles of at least 0.1 micron and no greater than 10microns. The press contains a fine mesh screen which makes the surface of the disc smooth. The smoothness of the disc provides for the readability of the assay. In a preferred embodiment, the disc has fibers which will trap latex particles, microspheres, or any other direct the flow of sample, tracer, and/or reagents down through the trap, or binder, zone rather than directing flow radially from the trap zone. This enables the assay to achieve maximal sensitivity.

In accordance with another embodiment, the absorbent may be made of a porous ceramic material. The ceramic absorbent may be defined as a non-fibrous, inorganic, porous matrix. The ceramic absorbent will have a uniform or identical porosity or density throughout the matrix which will enable the ceramic absorbent to retain non-charged particles having a size of at least 0.1 micron and no greater than 10 microns. The ceramic absorbent may have a pore size which preferably is from about 0.5 micron to about 10microns. Preferably, the ceramic absorbent has a uniform porosity which is from about 10% to about 80%, most preferably at about 40%.

The porous ceramic absorbent is microporous throughout, and no macropores are present. The porous ceramic absorbent, in a preferred embodiment, is a unitized structure molded as a unitary piece. The absorbent may be made from an aluminum oxide-containing material, such as alumina.

The porous ceramic absorbent may be produced from a raw material containing alumina with a range of purity of from about 50% to about 99.9%. The alumina is milled to a uniform particle size and is then spray dried. Subsequent to spray drying, the uniform alumina is mixed with binders, release agents, and/or microparticles to produce a uniform powder. Suitable microparticles are those which will burst upon firing of the ceramic, thereby leaving pores in the ceramic material. Examples of such microparticles include latex microparticles. The powder may then be processed in a number of ways to produce greenware. Examples of such processing include extrusion into rods, roll pressing into thin sheets, or pill pressing to form any design, or injection molding to form any design. Preferably, the powder is pill pressed.

The shape of the absorbent can vary depending upon the design of the mold used in the pill pressing operation. The composition of the alumina, the binders, the amount of material used and the pressing pressure will affect the porosity of the final product. The higher the pressing pressure and/or the firing temperature, the less porous the absorbent will be. The greenware is fired at a temperature effective to harden the greenware. Preferred firing temperatures are from about 1,000° C. to about 1,500° C. During the firing process, the binders, release agents, and microparticles vaporize out of the alumina matrix, whereby pores are produced in the hardened ceramic. The temperature of the firing will affect the shrinkage of the absorbent and the porosity of the final ceramic absorbent product. The ceramic absorbent, after firing, may be evaluated for porosity using flow rate analysis, water saturation tests, and mercury intrusion porosity tests. It is to be understood that the contact time of a sample with the surface of the ceramic absorbent is dependent upon the pore size of the absorbent. A larger pore size of the absorbent provides for a faster flow of the sample through the absorbent and less contact time of the sample with the surface of the absorbent, whereas a smaller pore size provides for a slower flow of the sample through the absorbent, and a greater contact time of the sample with the surface of the absorbent. To provide for the optimum contact time of the sample with the surface of the absorbent, the ceramic absorbent preferably has a pore size of from about 0.5 micron to about 10 microns, as hereinabove stated. The flow rate may also be adjusted by varying the pressing pressure and/or the firing temperature to accommodate a variety of assay conditions and contact times.

In accordance with yet another aspect of the present invention, the absorbent material may further include a plurality of fibers interspersed throughout the absorbent material. The fibers are parallel to each other and to the direction of flow of a sample when a sample is applied to the surface of the absorbent. Preferably, the fibers are located adjacent to the pores of the absorbent. The fibers thus aid in directing the flow of sample through the trap or binder zone, rather than directing flow radially from the trap zone. Such an embodiment is particularly useful when the absorbent is divided into plurality of test zones because the fibers aid in preventing cross-flow of the samples.

When a porous plastic or ceramic absorbent is employed, the fibers preferably are silica fibers coated with a ceramic material. When a pressed fiber disc, as hereinabove described, is employed, the disc may contain cellulosic fibers which are parallel to each other and to the direction of flow of the sample.

In accordance with the present invention, one can conduct an assay by placing a binder for an analyte (antigen, hapten, or antibody) on at least a portion of the surface of the absorbent. The binder may be placed on the surface of the absorbent in the form of a spot or dispensed, sprayed, or printed onto the membrane surface to produce symbolic forms. The binder may be placed directly on the surface of the support (either by passive or covalent methods of attachment) or may be supported on solid particles, e.g., latex particles which are placed on the surface of the absorbent. The surface of the absorbent is then contacted with a sample suspected of containing an analyte. The binder which is supported on the surface of the absorbent material is specific for the analyte. Any analyte present will bind with the binder on the surface of the absorbent material and form an analyte-binder complex. The surface of the absorbent is also contacted with a tracer simultaneously with or subsequent to contact with the sample. The tracer is a labeled form of a ligand and the ligand employed is dependent on the assay format. In a competitive assay, the ligand of the tracer is one which is bound by the binder for the analyte. In a sandwich assay, the ligand of the tracer is bound by the analyte (direct assay) or bound by a binder for the analyte (indirect assay). When a sandwich assay is employed, the tracer is preferably a labeled form of a ligand which is specific for the analyte. In the assay, the analyte and tracer become bound to the supported binder (the tracer is directly bound to supported binder in a competitive assay and bound to the supported binder through the analyte in a sandwich assay) and therefore remain on the surface of the support. The binding occurs while flowing the sample and tracer past the supported binder and any unbound portions flow into the absorbent by means of capillary movement through the absorbent. Typical flow rates, for example, may be from about 12 sec./ml to about 40 sec./ml, although the invention is not to be limited thereby.

After one or more of the steps, one may wish to wash the surface which supports the binder, prior to a subsequent step. For example, in the case of a sandwich assay, the surface may be washed subsequent to sample addition and prior to tracer addition and/or subsequent to tracer addition and prior to development thereof. The wash may contain standard aqueous buffers; eg., phosphate and Tris buffers. The wash may also contain detergents and chaotropic agents to minimize nonspecific binding.

The method of determination of analyte in the assayed sample depends upon the type of marker used in conjunction with the ligand or tracer. If a dye is used as a label or marker, it will appear on the surface of the absorbent and remain on the surface of the absorbent following any washing steps. In an enzyme label, a suitable substrate is used to provide color. The presence of radioactive, fluorescent, chemiluminescent, enzyme, chromogen, spin label, biotin, gold particles or other types of markers which remain on the surface of the absorbent material can be determined by any means known in the art.

The assay may be a qualitative or a quantitative assay, and the term "determining" as used herein means qualitative and/or quantitative determining of analyte.

Representative examples of assays for specific analytes include assays for mononucleosis heterophile antibodies and for Group A Streptococcus. In an example of an assay for mononucleosis heterophile antibodies, a specimen suspected of containing mononucleosis heterophile antibody which is dispensed onto the surface of the absorbent material containing the binder or antigen and flows past the binder before being absorbed into the support. The binder can be bound (either by passive or covalent methods) to a particle (i.e., latex) coated on the absorbent surface, or bound directly to the absorbent surface, or bound directly to the absorbent material by a passive or covalent process. The mononucleosis heterophile antibodies, when present, will be trapped to the binder (purified mononueleosis antigen). The tracer, which may be anti-human IgM or anti-human IgG, is then dispensed onto the surface and will bind to the human IgM or IgG heterophile antibodies bound to the binder. The tracer can be labeled with a variety of detectable markers such as a radioactive isotope, of, for example, iodine, cobalt or tritium, enzymes, fluorescent dyes, absorbing dyes, metals, chemiluminescent substances, spin labels, biotin, gold particles or any other labeling substance known to one of ordinary skill in the art. If heterophile antibodies are not present in the specimen, detectable levels of the tracer will not bind to the absorbent surface. Unbound tracer can be removed using a wash step. The wash step may require the use of a combination of detergents and chaotropic agents to minimize nonspecific binding to the surface of the absorbent parts. A wash step may also be omitted from the assay depending upon the signal to noise ratio. For example, dye based systems can use conjugates in a diluted form in a sufficient volume so as to increase this ratio. In enzyme based systems, the conjugate and/or substrate can double as a washing mechanism. With tracers made from dye conjugates, the reactions can be visualized immediately after the wash buffer is absorbed into the device. If an enzyme is used as the tracer, the addition of an enzyme substrate produces a colored product which will be visualized on the surface of the absorbent device. In the absence of mononucleosis antibodies, the labeled antibody will not bind to the binder. In this case, the enzyme will not be bound to the surface and will not generate a colored product.

In an example of an assay for Group A Streptococcus, a specimen swab suspected of containing Group A Streptococcus is suspended in an extraction buffer (i.e., chemical or enzymatic) known to one of ordinary skill in the art. After a brief period of incubation, the Group A specific carbohydrate antigens are exposed, the extract can be neutralized to improve the binding of antigen to antibody. A portion of the extract is applied to the surface of the absorbent material which contains a binder. The binder can be bound to a particle (i.e., latex or other appropriate microsphere) coated on the absorbent surface, or bound directly to the absorbent material by a passive or covalent process. The binder may be purified polyclonal antibody prepared against the Group A specific carbohydrate antigen. As the extract passes by the binder, the Group A antigen, when present, will be trapped by the binder containing antibody. The tracer, which can be a polyclonal or monoclonal antibody specific for the Group A carbohydrate, is then dispensed onto the absorbent material and allowed to absorb into the device. The tracer, in this instance, can be labeled with a variety of detectable markers such as described above or any other labeling substance known to one of ordinary skill in the art. If Group A antigens are not present in the extract, detectable levels of the tracer will not bind to the absorbent surface. Unbound tracer can be removed using a wash step as described above. The wash step may require the use of a combination of detergents and chaotropic agents to minimize nonspecific binding to the surface of the absorbent parts. With tracers made from dye conjugates, the reactions can be visualized immediately after the wash buffer is absorbed into the device. If an enzyme is used as the tracer, the addition of an enzyme substrate produces a colored product which will bind to the surface of the absorbent device. In the absence of Group A Streptococcus antigen the labeled antibody will not bind to the binder. In this case the enzyme will not be bound to the surface and will not generate a colored product.

The following example will illustrate an embodiment of the formation of a porous plastic support and an assay employing this support, in accordance with the present invention.

EXAMPLE

A porous plastic support is prepared from a mixture of liquefied polyethylene and a surfactant. The liquefied polyethylene and surfactant mixture becomes shaped into a cylindrical plastic support having an approximate pore size of from about 5 microns to about 30 microns. A slurry of cellulose acetate is then added to the surface of the plastic support. The cellulose acetate becomes absorbed into the plastic support and is allowed to dry. The cellulose acetate is added in an amount so as to provide pore sizes on the support of from about 0.1 to about 10 microns.

The plastic support, which is hydrophobic, is then contacted with Verion surfactant. The surfactant is added to the surface of the support, whereby the support is impregnated with the surfactant so as to produce a hydrophilic surface.

The solid support is prepared for use in conjunction with a mononueleosis assay as follows:

Polystyrene latex particles are covalently coated with mononucleosis antigen prepared from bovine cells. The mononucleosis antigen employed in this example was purchased from Meridian Diagnostics. The latex particles are then placed on a portion of the surface of the solid support. Polystyrene latex particles which are passively coated, or loaded, with human IgM are then placed on another portion of the solid support. This portion intersects the portion of the support where the polystyrene latex particles coated with mononucleosis antigen were placed. The zones of placement of the latex particles coated with mononuleosis antigen and of the polystyrene latex particles coated with human IgM are in the form of a plus "+" sign.

The surface of the porous plastic support is then contacted with 0.5% goat serum so as to prevent non-specific adsorption.

The assay is then conducted as follows:

150 µl of human serum is placed on the surface of the porous plastic support and adsorbed into the support. Then, 100 μl of colloidal gold, conjugated to goat anti-human IgM, is placed on the porous plastic support. 250 to 500 μl of 1M guanidine and 5% Triton - X wash buffer are then added. The surface of the porous plastic support is then read in order to determine the presence of mononucleosis antibody. If mononucleosis antibody is present in the sample, the conjugate of colloidal gold and goat anti-human IgM will bind to the mononucleosis antibody which is bound to the mononucleosis antigen, as well as to the human IgM. A plus "+" sign will appear on the surface of the support. If mononucleosis antibody is not present in the sample, the conjugate will bind only to the human IgM, and a minus "+" sign will appear on the surface of the support.

In some cases it may be possible to use the porous material in an assay without a binder for the analyte. In such cases, the analyte is retained on the surface of the porous absorbent material; e.g., porous plastic. The tracer is also applied to the porous plastic and becomes bound to analyte if present. The presence and/or amount of analyte is then determined by the presence of tracer on the surface.

It is to be understood, however, that the scope of the assay of the present invention is not to be limited to the specific embodiments described above. The invention may be practiced other than, as particularly described and still be within the scope of the accompanying claims.

What is claimed is:

1. A device comprising:

a porous ceramic absorbent material, said porous ceramic absorbent material being microporous throughout and being free of macropores, and said porous ceramic absorbent material having a uniform porsity throughout said material to enable said material to retain non-charged particles having a size of at least 0.1 micron and no greater than 10 microns.

2. The device of claim 1 wherein said porous ceramic absorbent has a pore size of from about 0.5 micron to about 10 microns.

3. The device of claim 1 wherein said porous ceramic absorbent is a unitary structure.

4. In an assay for an analyte wherein a sample containing analyte is applied to an absorbent material and an analyte is determined, the improvement comprising:

applying sample containing analyte to a surface of a porous ceramic absorbent material being microporous throughout and being free of macropores, and said porous ceramic absorbent material having a uniform porosity throughout said material to enable said material to retain non-charged particles having a size of at least 0.1 micron and no greater than 10 microns and determining analyte retained on said surface.

5. The assay of claim 4 wherein said assay is a competitive assay.

6. The assay of claim 4 wherein said assay is a sandwich assay.

7. The assay of claim 4 wherein said assay is an ELISA assay.

* * * * *